United States Patent [19]
Plechinger et al.

[11] Patent Number: 5,318,518
[45] Date of Patent: Jun. 7, 1994

[54] IRRIGATING CATHETER

[75] Inventors: Hans Plechinger, Neusaess; Josef Koehler, Aachen, both of Fed. Rep. of Germany

[73] Assignee: HP Medica Gesellschaft mbH fur Medizintechnische Systeme, Augsburg, Fed. Rep. of Germany

[21] Appl. No.: 926,746

[22] Filed: Aug. 7, 1992

[30] Foreign Application Priority Data

Aug. 14, 1991 [DE] Fed. Rep. of Germany ....... 4126886

[51] Int. Cl.⁵ .............................................. A61M 3/00
[52] U.S. Cl. ......................................... 604/43; 604/35; 604/22
[58] Field of Search ................. 604/35, 39, 43, 19, 604/27, 44, 45, 40, 41, 42, 22; 128/66

[56] References Cited

U.S. PATENT DOCUMENTS

| | | | |
|---|---|---|---|
| 1,902,418 | 3/1933 | Pilgrim | 604/43 |
| 2,460,473 | 2/1949 | Smith | 604/43 |
| 2,564,809 | 8/1951 | Levene | 604/45 |
| 3,916,909 | 11/1975 | Kletschka | 604/35 |
| 4,061,146 | 12/1977 | Bachr et al. | 604/22 |
| 4,468,216 | 8/1984 | Muto | 604/43 |
| 4,690,672 | 9/1987 | Veltrup | 604/43 |
| 4,715,848 | 12/1987 | Beroza | 604/35 |
| 4,913,698 | 4/1990 | Ito et al. | 604/35 |
| 5,058,570 | 10/1991 | Idemoto et al. | 604/22 |
| 5,061,255 | 10/1991 | Greenfeld et al. | 604/22 |
| 5,084,013 | 1/1992 | Takase | 604/43 |

FOREIGN PATENT DOCUMENTS

| | | |
|---|---|---|
| 0175096A1 | 3/1986 | European Pat. Off. . |
| 0232678B1 | 8/1987 | European Pat. Off. . |
| 331313 | 9/1989 | European Pat. Off. ............... 604/22 |
| 0377051A1 | 7/1990 | European Pat. Off. . |
| 0387755A1 | 9/1990 | European Pat. Off. . |
| 0390993A1 | 10/1990 | European Pat. Off. . |
| 0411170A1 | 2/1991 | European Pat. Off. . |
| 04425579A1 | 8/1991 | European Pat. Off. . |
| 1616003 | 5/1971 | Fed. Rep. of Germany . |
| 2430158 | 1/1976 | Fed. Rep. of Germany . |
| 2438648A1 | 2/1976 | Fed. Rep. of Germany . |
| 2447513A1 | 4/1976 | Fed. Rep. of Germany . |
| 3421390A1 | 12/1985 | Fed. Rep. of Germany . |
| WO90/05493 | 5/1990 | PCT Int'l Appl. . |
| 1648405A1 | 5/1991 | U.S.S.R. . |

Primary Examiner—John G. Weiss
Attorney, Agent, or Firm—Darby & Darby

[57] ABSTRACT

The downstream end section of a transporting lumen (4) for the irrigating fluid is constructed as a nozzle (14), which directs a strong, sharp jet over a free segment (130) into the inlet (16) of a discharging lumen (6). The irrigating fluid jet produces a suction effect, by means of which it aspirates the material from the treated organ (8) and discharges it through the discharging lumen (6). To intensify the suction effect of the irrigating fluid jet, the discharging lumen, when viewed from its inlet (16), consecutively contains the following elements: a mixing tube (18), a diffuser (20) and a discharging duct (22).

12 Claims, 3 Drawing Sheets

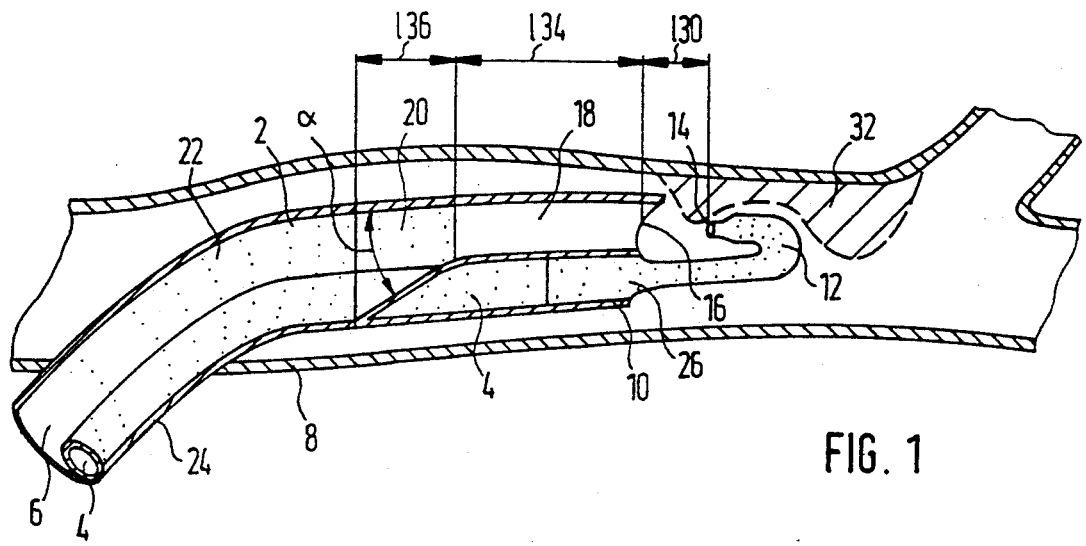
FIG. 1
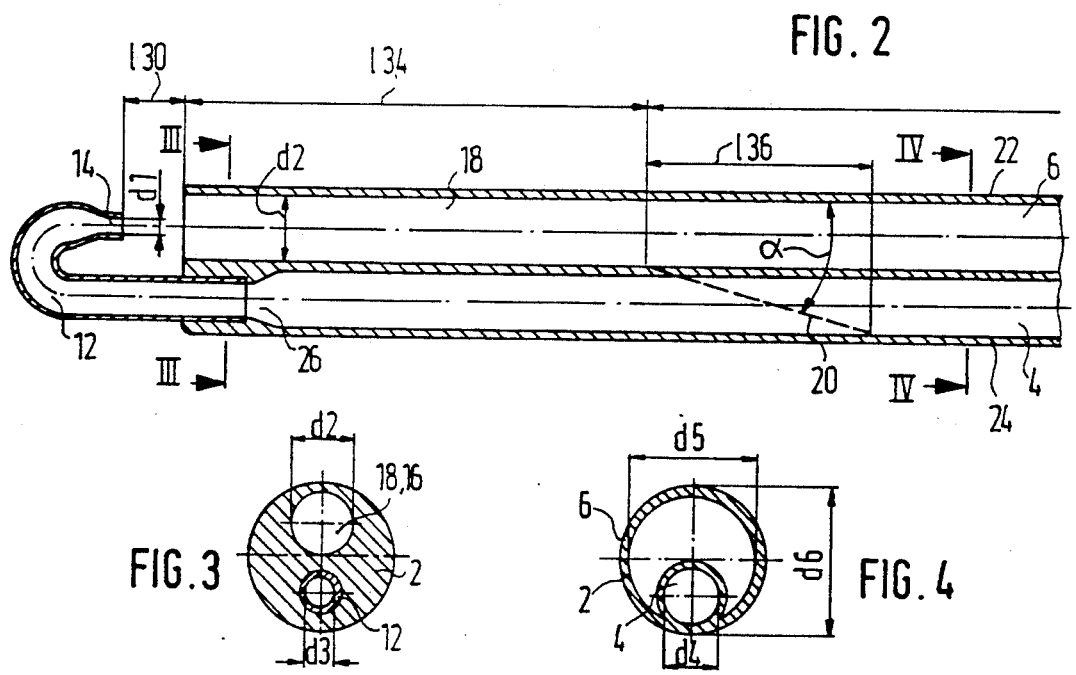
FIG. 2
FIG. 3
FIG. 4
FIG. 5
FIG. 6

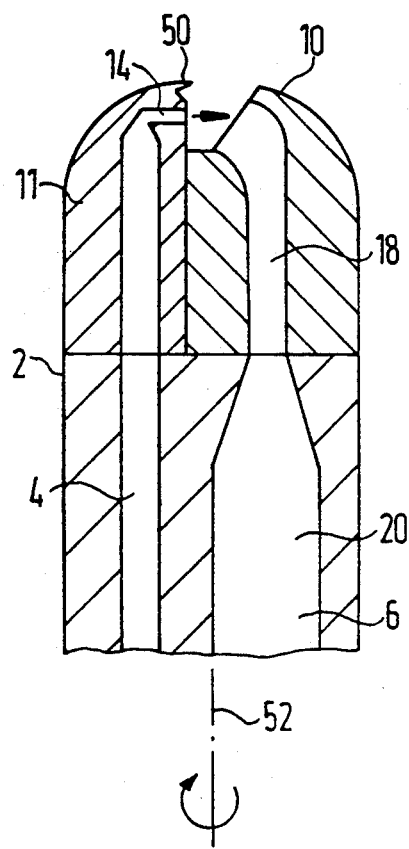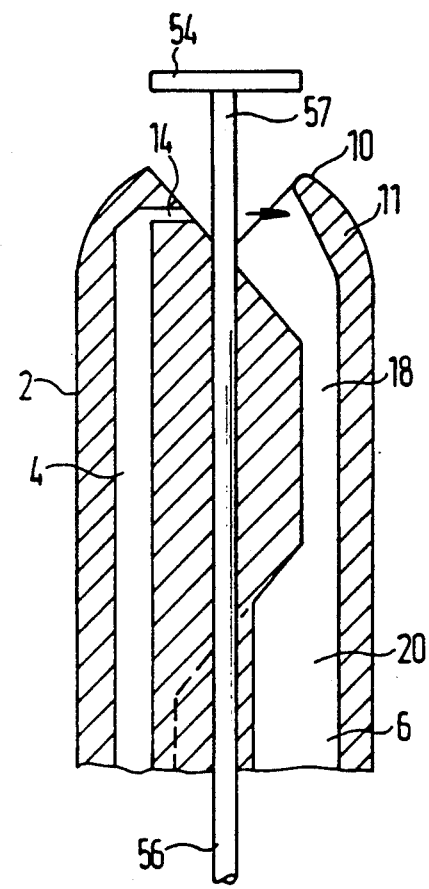

IRRIGATING CATHETER

The disclosure of German Patent Application No. P4126886.5, filed Aug. 14, 1991 is incorporated herein by reference.

FIELD OF THE INVENTION

The invention relates to an irrigating catheter for eliminating solids from body organs and hollow body organs or cavities of man and animals.

BACKGROUND OF THE INVENTION

With many catheters, the irrigating fluid preferably is a liquid. Such an irrigating catheter is disclosed in the European patent 0 175 096, the U.S. equivalent of which is U.S. Pat. No. 4,690,672. A liquid is supplied with a pressure of up to 30 bar to the transporting lumen of this irrigating catheter. In the region of the nozzle, the liquid still has a pressure of 5 to 20 bar. The nozzle is formed in a section of the transporting lumen, which protrudes tongue-like, axially removed, above the inlet of the discharging lumen. Under the action of the jet of liquid emerging from the nozzle, solids can be broken up or deposits dissolved in a patient's organ or body cavity. Under the action of a negative pressure in the suction duct, which is connected to a source of suction, the debris is drawn into this suction duct. The transport into and through the suction duct is supported by the jets of liquid emerging from the nozzle as well as from further openings of the transporting lumen. The nozzle can be axially displaceable so that its distance from the inlet of the discharging lumen can be adapted to the size of the solid that is to be discharged from the organ. A similar irrigating catheter, in which, however, the nozzle of the transporting lumen has the shape of a hook that is bent in the direction of the inlet, is disclosed in U.S. Pat. No. 1,902,418.

It is an object of the invention to provide an irrigating catheter constructed such that deposits, tumors and foreign material can be removed and transported from body organs and hollow body cavities, such as arteries, veins, cavities of the heart, cavities of the nose, bronchia, bladders, etc. of man and animals without damaging vascular walls and tissues during the comminution and transporting away of the material.

It is another object that the catheter be capable of aspirating mucus and foreign material from the tracheobronchial tree and removing and transporting away deposits and thrombi from blood vessels.

It is a further object that the irrigating catheter exhibit a high degree of operational safety, is easy to handle and has a low production price, so that it is also suitable as a disposable article.

SUMMARY OF THE INVENTION

By means of a diffuser of the inventive irrigating catheter, a strong suction action is achieved at the inlet of the discharging lumen, causing the break up and transportation of solids from the organ in question. According to the invention, an irrigating catheter of small volume can treat a large region in the organ. It is an advantage of the invention that a suction source need not normally be connected to the discharging lumen and that, when one is needed, the suction source can have a suction power significantly lower than that of known irrigating catheters. The irrigating fluid, preferably a liquid, can be supplied with a pressure of more than 150 bar to the transporting lumen.

The nozzle is constructed and positioned away from the discharging lumen such that negative pressures without backstreaming develop in the fluid jet between said nozzle and said inlet. Particularly due to the diffuser contained in the discharging lumen, the nozzle, together with the discharging lumen, forms a jet apparatus with a particularly good suction action, because the fluid jet of the nozzle does not significantly expand before the inlet of the discharging lumen, but flows past the inlet. By means of the sharp fluid jet or liquid jet, which emerges from the nozzle as if it were an ejector and is collected by the inlet of the discharging lumen, the following effects are achieved:

a) a suction effect
b) a comminuting (shredding, breaking up and dissolving) and
c) a transporting action (back transport of the irrigating fluid together with the material entrained by the irrigating fluid in the organ.

Aspiration carries the material from the organ into the vicinity of the comminuting region at the inlet of the discharging lumen. After the comminution, the mixture of irrigating fluid and comminuted material is conveyed out of the organ through the discharging lumen. With only a slight stress and without serious risk for the patient, constrictions and obstructions can be removed from the vascular system with the inventive irrigating catheter without any residues remaining behind. To begin with the heart and the extremities are in the foreground as the most important areas of application. The irrigating catheter is, however, also suitable for the intraoperative treatment in hollow organs and cavities, on teeth and on the skin. As the irrigating fluid, liquids, such as suspensions, are preferably used. However, depending on the intended application, it is also possible to use gases. The irrigating catheter can be used manually or in a partially automated or fully automated fashion.

BRIEF DESCRIPTION OF THE DRAWINGS

The foregoing and other objects and advantages of the present invention will become apparent to those skilled in the art upon reading the detailed description of the preferred embodiments in conjunction with a review of the appended drawings, in which:

FIG. 1 shows a longitudinal section through an artery with an inserted, inventive, irrigating catheter;

FIG. 2 shows a longitudinal section of the irrigating catheter of FIG. 1 in a different representation;

FIG. 3 shows a cross section along the plane III—III of FIG. 2;

FIG. 4 shows a cross section along the plane IV—IV of FIG. 2;

FIG. 5 shows a cross section of a further embodiment of an inventive irrigating catheter along the plane III-—III of FIG. 2;

FIG. 6 shows a cross section of the embodiment of FIG. 5 along the plane VI—VI of FIG. 2;

FIG. 7 shows a longitudinal section of a front end section of a further embodiment of an inventive irrigating catheter;

FIG. 8 shows a front, end section in longitudinal section of a yet further embodiment of an inventive irrigating catheter.

DETAILED DESCRIPTION OF THE PREFERRED EMBODIMENTS

Figure 9:
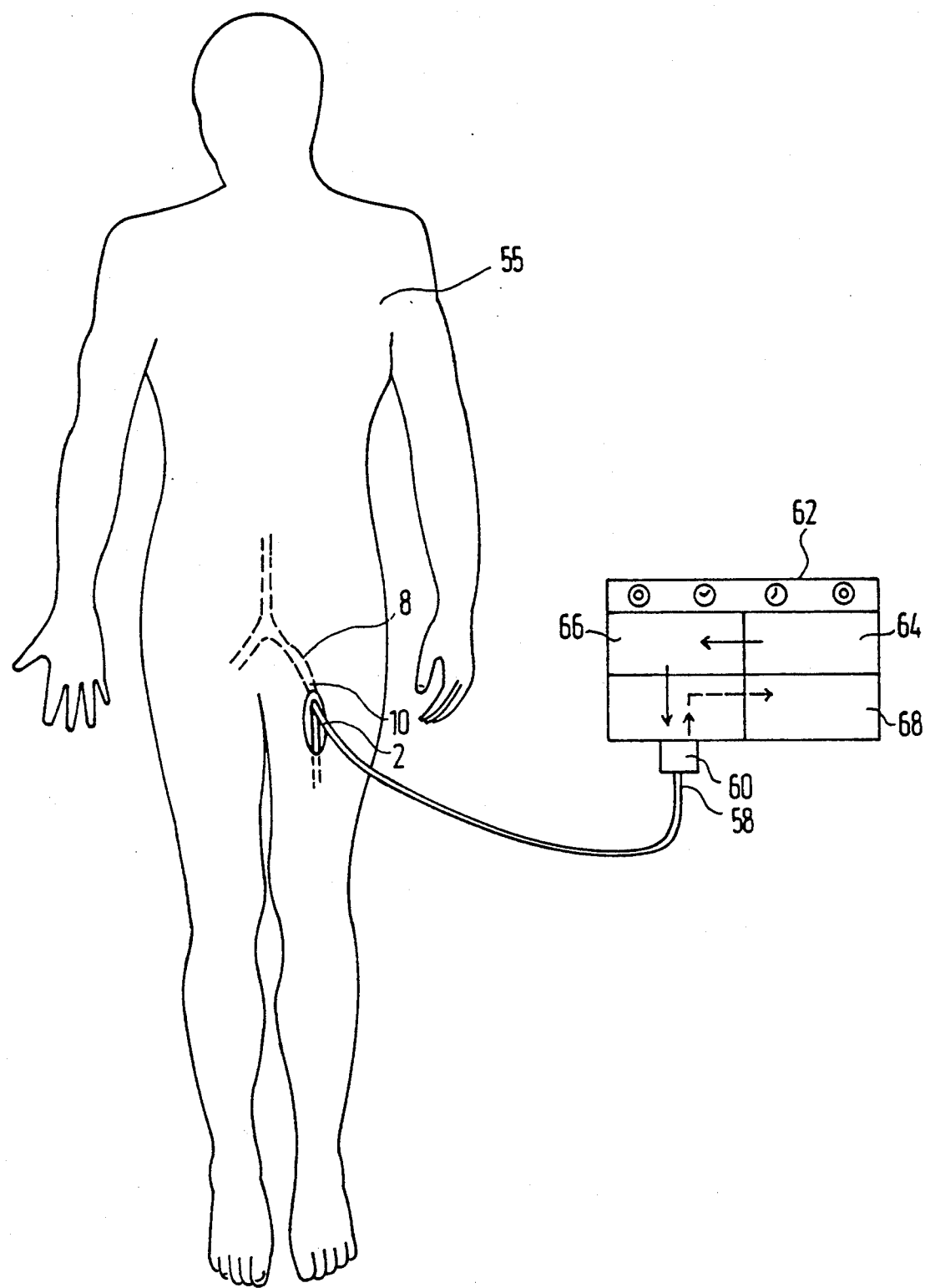
FIG. 9 shows the use of the irrigating catheter of FIGS. 1 to 4 in fully automatic operation.

FIGS. 1 to 4 show an irrigating catheter 2, which has two lumens 4 and 6 and is introduced into a body vessel 8, for example, an artery. One lumen 4 is a transporting lumen for supplying irrigating fluid, particularly a liquid, to the front end 10 of the irrigating catheter 2, where the transporting lumen 4 is provided with an elbow 12, which is bent back at an angle of 180° and at the end of which a nozzle 14 is provided. The irrigating liquid flows from the transporting lumen 4 out of the nozzle 14 in the form of a sharp jet axially into the front end inlet 16 at the front end of the discharging lumen 6. The pressure of the irrigating fluid at the nozzle 14 can be as high as 150 bar. The discharging lumen 6 consists of the following consecutive sections, a cylindrical mixing tube 18 forming the inlet 16, a diffuser 20 that is connected downstream and a recirculating duct 22 or a recirculating pipeline 22. The transporting lumen 4 and the discharging lumen 6 are disposed one inside the other with parallel axes and are mutually offset. They may be integrally formed or constructed from separate pieces. Preferably, the mixing tube 18 and the diffuser 20 together consist of a single piece and the elbow 12 and the nozzle 14 consist of a single piece. The one-piece section of mixing tube 18 and diffuser 20 is connected, to the recirculating line 22, preferably by gluing or welding. The one-piece part of elbow 12 and nozzle 14 is inserted in the section of the transporting lumen 4 forming a transporting pipeline 24, preferably with gluing or welding. The nozzle 14 is formed by a reduced-diameter section. Upstream from the elbow 12, the elbow-nozzle part 12, 14 preferably contains an additional nozzle section 26, the cross section of which tapers in the flow direction. Due to this double decrease in cross section in the first nozzle section 26 and in the subsequent nozzle 14, a very thin, sharp fluid jet is formed. The distance 130 between the outlet end of the nozzle 14 and the inlet 16 of the discharging lumen 6 or its mixing tube 18 is sufficiently large, so that the sharp fluid jet does not disperse in this distance 130, but can shred or shatter the tissue 32 of the vessel 8 lying between and drive the shattered material particles into the inlet 16. The vessel 8 can also be described as a hollow organ or cavity. The irrigating catheter can, however, also be introduced into solid organs of man or animals. The length 134 of the mixing tube and the length 136 of the diffuser, as well as the aperture angle of the diffuser 20 are matched to one another and to the size of the fluid jet emerging from the nozzle 14, so that the action of the diffuser 20, due to the irrigating fluid in the mixing tube 18, brings about a reinforcement of the suction action of the jet, which flows from the nozzle 14 into the inlet 16 of the mixing tube 18.

The impulse of the irrigating fluid jet, which leaves the orifice 14 and flows into the inlet 16 and consists, for example of an isotonic salt solution and/or air and has a flow volume of $Q_t$, is transferred by friction and turbulence partly to the surrounding medium within the distance 130 and brings about the aspiration of a suction flow volume $Q_s$. This suction effect is used to remove material from the vessel 8 or a different hollow organ, such as mucus from the bronchia or thrombi 32 from blood vessels 8. The irrigating fluid jet of nozzle 14, in addition to generating this effect, can also be used to shatter or shred or dissolve solid material in the organ 8 in question. The total volume stream, which is discharged from the body through the discharging lumen 6 of the catheter 2, then has the volume $Q_g = Q_t + Q_s$. In the drawings, d1 is the diameter of the preferably circular internal cross section of the nozzle 14, d2 is the diameter of the preferably circular flow cross section of the inlet 16 and of the mixing tube 18, d3 is the diameter of the preferably circular internal flow cross section of the elbow 12 and of the flow cross section of the transporting lumen 4, which is directly upstream from the elbow 12 in the sectional plane III—III and is downstream of the first nozzle section 26, d4 is the diameter of the circular flow diameter of the transporting lumen 4 in its section, which forms a transporting line 24 and is upstream from the first nozzle section 26; d5 is the internal diameter of the circular flow cross section part of the discharging lumen 6 in its section 22 forming a recirculating line downstream from the diffuser 20, and d6 is the external diameter of the irrigating catheter 2, which preferably is circular on the outside. Since the transporting lumen 4 is disposed within the discharging lumen 6 offset parallel to the axis of the latter, the transporting lumen 4 has a circular internal cross section. However, the discharging lumen 6 has a half moon-shaped internal cross section, corresponding to FIG. 4 at the sectional plane IV—IV of FIG. 2.

The irrigating catheter of this type has the advantage that it is still effective even if it is produced with very small dimensions. Preferably, the ratio d1/d2 of the internal diameter d1 of the nozzle 14 to the internal diameter d2 of the mixing tube 18 and its inlet 16 should fall within the range of 0.2 to 0.7. The ratio 130/d2 of the distance 130 of the nozzle 14 from the inlet 16 of the mixing tube 18 to the internal diameter d2 of the mixing tube 18 and its inlet 16 should lie between 0.3 and 1.5. The ratio 134/d2 of the length 134 to the internal diameter d2 of the mixing tube 18 should be between 2.5 and 8.2. Finally, the aperture angle $\alpha$ of the diffuser 20 should be between 2° and 30°.

A further embodiment of an irrigating catheter according to the present invention is represented in FIGS. 5 and 6, in which the catheter contains more then two lumens 4 and 6. For example, a lumen 40 may be provided for measuring the pressure in the organ 8 that is to be treated, and a lumen 42, in which additional treating equipment, such as a pressure-measuring element, an ultrasonic head or a laser head can be disposed at the front end 10.

The function of the irrigating catheter is to form a jet-suction device. The diffuser 20 brings about a pressure recovery in the discharging lumen 6 and, with that, supports the recirculation of the irrigating fluid and the discharge of the material that is carried along in the irrigating fluid from the treated organ 8. The diffuser 20 brings about a reduction in the pressure loss in the discharging lumen 6 and furthermore an increase in the suction flow ratio $q = Q_s/Q_t$ and an increase in the efficiency. The ratio of the diffuser cross section at its upstream start to the diffuser cross section at its downstream end has a decisive effect on the suction characteristics and the efficiency. Because of its friction, the irrigating fluid jet between the orifice 14 and the inlet 16 of the mixing tube 18 entrains material from its surroundings and produces a negative pressure in the region of the distance 130. Over the irrigating fluid flow in the discharging lumen 6, the pressure at the inlet 16 is in equilibrium with the pressure at the downstream end of the discharging lumen 6, where the material entrained in the irrigating fluid reaches a collecting container. The collecting container normally is vented and thus is at atmospheric pressure. The pressure at the inlet 16 of the mixing tube 18 is above or below atmospheric pressure by an amount equal to the sum of all pressure losses and pressure recoveries. To make the pressure below atmospheric, the pressure recovery in the discharging lumen 6 must be sufficiently large. The negative pressure, required in the organ 8 that is to be treated, arises in the aforementioned manner due to the irrigating fluid jet of the nozzle 14 and due to the diffuser 20. Admittedly, there is a pressure recovery due to the expansion of the cross section of the irrigating fluid jet from the nozzle 14 as the irrigating fluid jet expands at the transition from the nozzle 14, which is small in cross section, to the mixing tube 18, which is larger in cross section. However, this pressure recovery is inadequate for achieving a satisfactory suction action in the treated organ 8. A sufficient suction effect is achieved only due to the additional action of the diffuser 20.

For the embodiments of FIGS. 7 and 8, parts that correspond functionally to those of FIGS. 1 to 6 have been provided with the same reference numbers. The essential difference in the embodiments of FIGS. 7 and 8 is that the nozzle 14 is disposed not at the end of an elbow 12, but in a symmetrical or asymmetrical fish mouth-like end section 11 of the irrigating catheter 2. FIG. 7 shows that a cutting edge 50 for cutting material in the organ 8 that is to be treated can be provided at the distal end of the irrigating catheter 2. For the cutting process, the irrigating catheter 2 can, for example, be rotated about its central axis of symmetry 52. It is evident from the embodiment of FIG. 8 that a rotary knife, which is fastened to the front end 10 of a shaft 56 that passes axially through the catheter 2, can also be provided as cutting tool 54. Instead of a cutting tool 54, a different implement, such as an optical viewing device, an ultrasonic device, a laser device, etc., can also be fastened to the front end 57 of the shaft 56.

FIG. 9 shows the practical application of the irrigating catheter 2, which is inserted with its front end 10 in an artery 8 of a patient 55. The rear end 58 of the irrigating catheter 2 or the feed lines of the latter are connected over a coupling 60 at a device 62 for the automatic treatment of an organ. The device 62 contains, for example, a reservoir 64 for the irrigating fluid, a pump 66, which pumps the irrigating fluid from the container 64 into the transporting lumen 4 of the catheter 2, and a collecting basin 68, in which the material, flushed out of the organ 8 by the irrigating liquid into the discharging lumen 6, is precipitated from the irrigating fluid and collected.

We claim:

1. An irrigating catheter for eliminating solids from body organs and hollow body cavities comprising:
    a catheter body having at least a first lumen and a second lumen, said first lumen being a transporting lumen for supplying an irrigating fluid from a high-pressure fluid source to an organ, said second lumen being a discharging lumen for discharging said irrigating fluid and said solids from the organ that have been entrained by the irrigating fluid;
    a nozzle formed at an outlet of the transporting lumen and disposed at a distance from and opposite to an inlet of the discharging lumen, said nozzle sending into said inlet an irrigating fluid jet, which engages said solids located between said nozzle and said inlet and discharges said solids through the discharging lumen;
    said discharging lumen having a mixing tube, an inlet of which is said inlet of the discharging lumen and in which said solid particles can disperse in the irrigating liquid, a diffuser and a discharging duct, the mixing tube and the diffuser being dimensioned such that the diffuser brings about an intensification of the suction effect of the irrigating fluid jet at the inlet of the mixing tube.

2. The irrigating catheter of claim 1, wherein said nozzle and said mixing tube have flow diameters, the ratio of the flow diameter of the nozzle at its outlet end to the flow diameter of the mixing tube being in the range 0.2 to 0.7.

3. The irrigating catheter of claim 2, wherein the distance from the nozzle to the inlet of the mixing tube is 0.3 to 1.5 times the flow diameter of the mixing tube.

4. The irrigating catheter of claim 3, wherein the length of the essentially cylindrical mixing tube is 2.5 to 8.2 times its flow diameter.

5. The irrigating catheter of claim 4, wherein the diffuser is divergent at an angle in the range 2° to 30°.

6. The irrigating catheter of claim 5, wherein the mixing tube and the diffuser consist of one piece of material, which is fastened to a section of the discharging lumen downstream thereof.

7. The irrigating catheter of claim 6, wherein means for cutting material in the organ is disposed at the distal end of the catheter.

8. The irrigating catheter of claim 7, wherein the nozzle is formed at a hook-like end section of the transporting lumen for the irrigating fluid.

9. The irrigating catheter of claim 7, wherein the distal end section of the irrigating catheter that is introduced into the organ is formed essentially as a symmetrical or asymmetrical fish-mouth head.

10. The irrigating catheter of claim 6, wherein a pressure measuring element is disposed at the distal end of the catheter.

11. The irrigating catheter of claim 6, wherein an ultrasonic device is disposed at the distal end of the catheter.

12. The irrigating catheter of claim 6, wherein a laser device is disposed at the distal end of the catheter.

* * * * *